(12) United States Patent
Couturier et al.

(10) Patent No.: US 9,221,745 B2
(45) Date of Patent: Dec. 29, 2015

(54) PROCESS FOR PREPARING AMINO ACIDS OR ESTERS COMPRISING A METATHESIS STEP

(75) Inventors: Jean-Luc Couturier, Lyons (FR); Jean-Luc Dubois, Millery (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/234,818

(22) PCT Filed: Jul. 27, 2012

(86) PCT No.: PCT/FR2012/051783
§ 371 (c)(1),
(2), (4) Date: Feb. 4, 2014

(87) PCT Pub. No.: WO2013/017786
PCT Pub. Date: Feb. 7, 2013

(65) Prior Publication Data
US 2014/0163196 A1 Jun. 12, 2014

(30) Foreign Application Priority Data
Aug. 2, 2011 (FR) .................................. 11 57065

(51) Int. Cl.
*C07C 227/04* (2006.01)
*C07C 253/32* (2006.01)
*C08G 69/08* (2006.01)

(52) U.S. Cl.
CPC ............. *C07C 227/04* (2013.01); *C07C 253/32* (2013.01); *C08G 69/08* (2013.01)

(58) Field of Classification Search
CPC .... C07C 253/30; C07C 227/04; C07C 255/23
See application file for complete search history.

(56) References Cited

U.S. PATENT DOCUMENTS

| | | |
|---|---|---|
| 2009/0264669 A1 | 10/2009 | Upshaw |
| 2010/0168453 A1 | 7/2010 | Dubois |
| 2011/0160472 A1* | 6/2011 | Lemke et al. ................. 554/154 |
| 2011/0224454 A1* | 9/2011 | Dubois ......................... 560/155 |
| 2011/0300590 A1 | 12/2011 | Dubois |

FOREIGN PATENT DOCUMENTS

| | | |
|---|---|---|
| CN | 1356311 A | 7/2002 |
| CN | 1596239 A | 3/2005 |
| EP | 0391639 A2 | 10/1990 |
| FR | 2 912 741 A1 | 8/2008 |
| FR | 2 938 533 A1 | 5/2010 |
| FR | 2938533 * | 5/2010 |
| FR | 2938533 A1 * | 5/2010 |
| FR | 2 941 694 A1 | 8/2010 |
| WO | WO 03/093215 A1 | 11/2003 |
| WO | WO 2009/020665 A1 * | 2/2009 |
| WO | WO 2009/020665 A1 | 2/2009 |
| WO | WO 2009/020667 A1 | 2/2009 |

OTHER PUBLICATIONS

Hampstead, Industrial and Engineering Chemistry, Destroying Peroxides of Isopropyl Ether, 1964, 56(6), pp. 37-42.*
International Search Report (PCT/ISA/210) mailed on Dec. 4, 2012, by the French Patent Office as the International Searching Authority for International Application No. PCT/FR2012/051783.
Weng Ganyou and Shi Jiangong (Xinye Technology Development Corp. of BYPC) "The Properties, Classification and Applications of Organic Peroxide" China Academic Journal Electronic Publishing House, p. 63-66 (2001).
Mudassar Abbas, Christian Slugovc, "As Low as Reasonably Achievable Catalyst Loadings in the Cross Metathesis of Olefins with Ethyl Acrylate", Tetrahedron Letters 52 (2011, p. 2560-2562, Elsevier.
Etienne Borre et al., "Design of a Library of Hoveyda-Grubbs Type of Olefin Metathesis Catalysts", Chemistry Today, vol. 27 No. 5, p. 74-78, Sep.-Oct. 2009, Chimica Oggi.
Office Action issued in Chinese Application 201280048366.5, Dec. 1, 2014.

* cited by examiner

*Primary Examiner* — Paul A Zucker
(74) *Attorney, Agent, or Firm* — Buchanan Ingersoll & Rooney P.C.

(57) ABSTRACT

A process for synthesizing a long-chain saturated α,ω-amino ester (acid) including from 6 to 17 carbon atoms, said process including a first step of cross metathesis between a first acrylic compound chosen from acrylonitrile, acrylic acid or an acrylic ester and a second monounsaturated compound including at least one nitrile, acid or ester trivalent function, one of these compounds including a nitrile function and the other an acid or ester function, in the presence of a ruthenium carbene metathesis catalyst, and a second step of hydrogenation of the monounsaturated nitrile-ester (acid) obtained, wherein said monounsaturated compound including at least one nitrile, acid or ester trivalent function has previously been subjected to a purification by thermal and/or chemical treatment.

16 Claims, No Drawings

PROCESS FOR PREPARING AMINO ACIDS OR ESTERS COMPRISING A METATHESIS STEP

The work which led to this invention received financing from the European Union as part of Framework Programme 7 (FP7/2007-2013) under project number 241718 EUROBIOREF.

The invention is directed to a process for synthesizing long-chain α,ω-aminoalkanoic acids or esters from a monounsaturated fatty acid or ester, comprising at least one metathesis step.

The polyamides industry, whether to manufacture synthetic fibers or thermosetting resins, uses a whole range of monomers consisting of diamines, dicarboxylic acids, and—especially—long-chain ω-amino acids. The latter are commonly called Nylons, defined by the length of methylene chain $(—CH_2)_n$ separating two amide functions —CO—NH—. Known accordingly are Nylon-6, Nylon-6-6, Nylon 6-10, Nylon 7, Nylon 8, Nylon 9, Nylon 11, Nylon 13, etc.

These monomers are generally manufactured by chemical synthesis using in particular, as starting materials, C2 to C4 olefins, cycloalkanes, or benzene, hydrocarbons obtained from fossil sources, but also, in certain specific cases, starting from castor oil (Nylon 11) or erucic oil (Nylon 13/13), or lesquerolic oil (Nylon 13).

Current developments in environmental matters are leading, in the fields of energy and chemistry, to a preference for exploitation of natural raw materials originating from a renewable source. This is the reason why some studies have been undertaken to develop, on the industrial scale, processes using fatty acids/esters as starting material for manufacture of these monomers.

There are only a few industrial examples of this type of approach. One of the rare examples of an industrial process utilizing a natural fatty acid as starting material is that for the manufacture, from ricinoleic acid, which is extracted from castor oil, of 11-undecanoic acid, which is the basis for the synthesis of Rilsan 11®. This process is described in the work "Les Procédés de Pétrochimie" by A. Chauvel et al., which appeared in Editions TECHNIP (1986). The 11-aminoundecanoic acid is obtained in a number of steps. The first consists of methanolysis of castor oil in a basic medium, producing methyl ricinoleate, which is subsequently subjected to pyrolysis to give, on the one hand, heptanaldehyde and, on the other hand, methyl undecylenate. The latter is converted into acid form by hydrolysis. The acid formed is subsequently subjected to hydrobromination to give the ω-brominated acid, which is converted by ammoniation to 11-aminoundecanoic acid.

In this "bio" route, the main studies have related to the synthesis of 9-aminononanoic acid, which is the precursor of Nylon 9, from oleic acid of natural origin.

As regards this specific monomer, it is possible to cite the work "n-Nylons, Their Synthesis, Structure and Properties"—1997, published by J. Wiley and Sons, in which section 2.9 (pages 381 to 389) is devoted to Nylon 9. This article summarizes the achievements with regard to and the studies carried out on the subject. Mention is made therein, on page 381, of the process developed by the former Soviet Union that resulted in the commercialization of Pelargon®. Mention is also made therein, on page 384, of a process developed in Japan that uses oleic acid from soybean oil as starting material. The corresponding description refers to the work by A. Ravve "Organic Chemistry of Macromolecules" (1967) Marcel Dekker, Inc., in which section 15 is devoted to polyamides, and which refers on page 279 to the existence of such a process.

The applicant has for its part carried out studies in this field. In the French patent application published under number FR 2912741, it described a process for synthesizing a whole range of amino acids/esters of this type from a long-chain natural fatty acid/ester, by subjecting the latter to a catalytic cross metathesis reaction with an unsaturated compound comprising a nitrile function, followed by hydrogenation. In the French patent application filed Nov. 17, 2008 under number FR0857780, it also described a process for synthesizing ω-aminoalkanoic acids or their esters from long-chain, unsaturated, natural fatty acids, passing via an intermediate ω-unsaturated nitrile compound, where one of the variant forms employs, in the final phase, a cross metathesis of the ω-unsaturated nitrile with an acrylate compound. Lastly, in the French patent application filed Feb. 5, 2009 under number FR0950704, it described a variant of the preceding process, in which the intermediate compound is of unsaturated dinitrile type. All these processes result in a final step of hydrogenation of the nitrile function and of the double bond.

An object of the process of the invention is to improve the performance levels of the processes for preparing amino acids or amino esters that comprise a metathesis step, by improving the step of purifying the starting materials, which has an effect, of course, on the final cost.

The aspect of purification of fatty acids or fatty esters for a metathesis process is described in patent application WO 03/093215. It is important for the process that the starting materials should as far as possible be free from poisons able to inhibit the metathesis catalyst. It is known that unsaturated fatty acid derivatives can undergo radical oxidation in air to give hydroperoxide and peroxide compounds, and that these organic peroxidic compounds are detrimental to metathesis catalysts. By purifying the reactants to eliminate these poisons and more particularly these hydroperoxides, it is possible to improve very significantly the activity of the metathesis catalysts as measured by the number of cycles ("turnover number"), which corresponds to the number of reactions carried out by one molecule of catalyst. In patent application WO 03/093215, the purification process prior to the metathesis reaction involves contacting the fatty acids or esters with a solid adsorbent such as activated alumina. This solution is effective in reducing the level of peroxides, typically from an initial value of the order of 300 meq/kg to a value of less than 1 meq/kg after treatment, allowing the turnover number of the metathesis catalyst to be increased from 0 to 2160.

Patent application US2009/0264669 also describes the use of solid adsorbents chosen, for example, from silicates, active carbons, and clays.

Employing an adsorbent, however, is a solution necessarily involving the use of a large quantity of adsorbent, and is costly in terms of the process since it requires investment in an adsorption column and requires a step of regenerating the adsorbent. It also leads to a loss of starting material, which remains trapped in the porosity on the solid material.

The applicant, however, has found that it is possible to carry out the metathesis process with very high turnover numbers by simply subjecting the fatty acid derivatives to a thermal and/or chemical treatment before using them for the metathesis reaction.

The invention provides a process for synthesizing a long-chain, saturated α,ω-amino ester (acid) comprising from 6 to 17 carbon atoms, said process comprising a first step of cross metathesis between a first, acrylic compound chosen from acrylonitrile, acrylic acid, or an acrylic ester, and a second, monounsaturated compound comprising at least one trivalent, nitrile, acid, or ester function, one of these compounds comprising a nitrile function and the other an acid or ester function, in the presence of a ruthenium carbene metathesis catalyst, and a second step of hydrogenation of the resulting monounsaturated nitrile-ester (acid), said monounsaturated compound comprising at least one trivalent nitrile, acid, or ester function having been purified beforehand by thermal and/or chemical treatment.

The metathesis reaction in question is a cross metathesis reaction between a monounsaturated acid or ester compound, generally obtained from oleochemistry, with acrylonitrile, or a cross metathesis reaction between an unsaturated nitrile compound, generally obtained from oleochemistry, with an acrylic, acidic, or acrylate compound, and in that case preferably methyl acrylate or butyl acrylate.

The process was developed for the purpose of exploiting starting materials originating from renewable natural sources. It may, however, also be applied effectively to similar monounsaturated compounds obtained by chemical synthesis. The metathesis step is carried out according to the following reaction scheme:

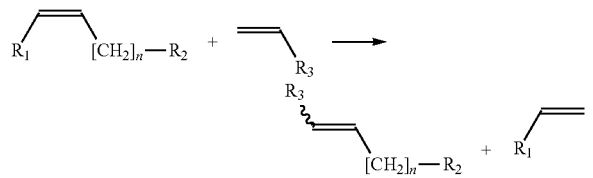

where $R_1$=H or $(CH_2)_m$—$R_4$,
$R_2$=COOR$_5$ or CN,
$R_3$=COOR$_5$ or CN,
$R_4$=H or $R_2$,
$R_5$=alkyl radical of 1 to 4 carbon atoms, or H,
n=2 to 13,
m=4 to 11, and
$R_2$ is identical to or different from $R_3$.

The abovementioned purification by chemical or thermal treatment is applicable to a process for preparing dicarboxylic acids, diesters, and/or dinitriles.

The formula of the final α,ω-amino ester (acid) synthesized depends essentially on that of the compound which reacts with the acrylic compound.

In this compound obtained from oleochemistry, i.e., obtained from renewable natural fatty esters or acids, $R_1$ is alternatively H, an alkyl radical, or a functional alkyl radical comprising a trivalent function (CN, COOH, or COOR).

$R_1$ will be H when the natural fatty ester is to be subjected, for example, to ethenolysis or, in certain cases, to pyrolysis. The formula of the resulting α,ω-amino ester/acid is then directly linked to the —$(CH_2)_n$-radical of the fatty ester. Accordingly, n will be 7 with oleic acid, 4 with petroselenic acid, 8 on the basis of ricinoleic acid subjected to pyrolysis, 10 on the basis of lesquerolic acid subjected to pyrolysis, etc., as is described in the French patent application published under number FR 2 912 741.

$R_1$ will be an alkyl radical when $R_4$ in $(CH_2)_m$—$R_4$ is H. This corresponds to the use in the process of a monounsaturated natural fatty acid such as, for example, oleic acid, palmitoleic acid, petroselenic acid, lauroleic acid, etc.

$R_1$ will be a functional alkyl radical when $R_4$ in $(CH_2)_m$—$R_4$ is a radical representing a trivalent CN, COOH, or COOR function, which will be identical to $R_2$. The compound in that case will be in the dicarboxylic acid, diester or dinitrile form.

It will then be particularly advantageous for the formula of the compound to have symmetry, allowing optimization of the yields of final α,ω-amino ester/acid. Obtaining this type of compounds, by metathesis in particular, is described in the above-cited patent applications FR 2912741, FR0857780, and FR0950704.

In one particular embodiment of the invention, with regard to the acrylic compound, the choice of the trivalent function $R_3$ may be linked to the nature of the trivalent function of the other compound, it being possible for $R_3$ to be nitrile when $R_2$ is ester/acid and, conversely to be ester/acid when $R_2$ is nitrile.

This reaction leads to unsaturated nitrile-acids or nitrile-esters.

The cross metathesis reaction of acrylonitrile is preferably carried out with a compound chosen from 9-decenoic acid or methyl 9-decenoate, which are obtained from the ethenolysis of oleic acid or of methyl oleate, or of a triglyceride containing oleic acid; 10-undecenoic acid or methyl 10-undecenoate, which are obtained from the cracking of ricinoleic acid or from methyl ricinoleate, oleic acid, or methyl oleate; 9-octadecenedioic acid or methyl 9-octadecenedioate, which are obtained from homometathesis or from the fermentation of oleic acid, erucic acid, and methyl erucate; 12-tridecenoic acid or methyl 12-tridecenoate, which are obtained from the thermal cracking of lesquerolic acid; 13-tetradecenoic acid or methyl 13-tetradecenoate, which are obtained from the ethenolysis of erucic acid, lesquerolic acid and methyl lesquerolate, gondoic acid or methyl gondoate; 11-dodecenoic acid or methyl 11-dodecenoate, which are obtained from the ethenolysis of lesquerolic acid or of gondoic acid.

The cross metathesis reaction of the acrylic ester (acid) is carried out with a compound chosen from 9-decenenitrile, which is obtained from 9-decenoic acid; 10-undecenenitrile, which is obtained from 10-undecenoic acid; 9-octadecenenitrile or oleonitrile, obtained from oleic acid, 9-octadecenedinitrile, obtained from 9-octadecenedioic acid or from the homometathesis of 9-decenenitrile, eruconitrile; 13-tetradecenonitrile, obtained from erucic acid; 12-tridecenenitrile, obtained from lesquerolic acid after a thermal cracking step, and 11-dodecenenitrile, obtained from lesquerolic or from gondoic acid after a step of ethenolysis.

The process for purifying monounsaturated compounds derived from fatty acids comprising a nitrile, acid or ester function, prior to the metathesis step, involves destroying the hydroperoxide and/or peroxide compounds by a thermal and/or chemical treatment.

The thermal treatment is carried out at a temperature of between 80° C. and 250° C., preferably between 80° C. and 180° C., in an inert atmosphere, for a time sufficient to decompose the hydroperoxide and/or peroxide compounds. The temperature is preferably between 100 and 200° C., or more preferably between 100 and 150° C. The thermal treatment is preferably carried out without solvent under a nitrogen atmosphere.

The chemical treatment comprises a step of adding a compound chosen from inorganic acids, bases, reducing agents, metals, metal salts, organic or inorganic compounds comprising ruthenium, and mixtures thereof, intended to decompose the hydroperoxide and/or peroxide compounds by reaction. The chemical treatment is preferably carried out without solvent, or in a solvent which is subsequently used for the metathesis step. The reaction takes place under conditions close to stoichiometry between the peroxide and the reactant in question.

The inorganic acids used are preferably chosen from sulfuric acid, perchloric acid, hydrochloric acid, and mixtures thereof, and are employed at a temperature of preferably between 20 and 50° C.

The bases used are preferably amines chosen from triethylamine, diethylamine, isobutylamine, triethanolamine, dimethylaniline, diethylaniline, dimethyl-para-toluidine, and mixtures thereof, and are employed at a temperature of preferably between 20 and 120° C.

The reducing agents used are preferably chosen from trialkyl- and triarylphosphines, particularly triphenylphosphine, trialkyl or triaryl phosphites, particularly triphenyl phosphite, inorganic or organic sulfides such as sodium hydrogensulfide, or thioxane, hydrazine, or alkyl- or arylhydrazines such as diphenylhydrazine, hydroxylamine, formic acid, oxalic acid, and mixtures thereof, and are employed at a temperature of between 20 and 50° C.

The metals used are preferably chosen from alkali metals, alkaline earth metals, and rare earths, aluminum, titanium, zirconium, zinc, tin, lead, bismuth, iron, nickel, cobalt, copper, silver, and mixtures thereof, and more particularly iron, nickel, cobalt, copper, silver, and mixtures thereof, and are employed at a temperature of between 20 and 150° C., and especially preferredly between 20° C. and 50° C. The most reactive compounds will be the alkali metals, then alkaline earth metals, then the rare earths, and, finally, the transition metals, silver being a less reactive compound.

The metal salts used are preferably chosen from iron derivatives, and preferably iron(II) acetate, iron(III) acetate, iron(II) acetylacetonate, iron(III) acetylacetonate, cobalt derivatives, and preferably cobalt(II) acetate, cobalt(II) acetylacetonate, cobalt(III) acetylacetonate, cobalt(II) 2-ethylhexanoate, copper derivatives, and preferably copper(I) acetate, copper(II) acetate, copper(I) acetylacetonate, copper (II) 2-ethylhexanoate, manganese derivatives, and preferably manganese(II) acetate, manganese(III) acetate, manganese (II) acetylacetonate, manganese(III) acetylacetonate, nickel derivatives, and preferably nickel(II) acetate, nickel(II) acetylacetonate, nickel(II) 2-ethylhexanoate, and mixtures thereof, and are employed at a temperature of between 20 and 100° C.

A possible example of a ruthenium-based compound is $Ru(NH_3)_6^{2+}$.

All of these treatments may reduce the hydroperoxide and or peroxide content of the monounsaturated compound derived from fatty acid to values of less than 3 meq/kg and preferably less than 1 meq/kg. Analysis of the concentration of hydroperoxide and/or peroxide in the reactants may be performed according to standard methods that are known to the skilled person, such as the method of titration with potassium iodide and sodium thiosulfate.

The cross metathesis reaction with an acrylic compound is carried out under conditions which are very well known. The metathesis reaction is preferably carried out at a reaction temperature of between 20 and 120° C., and the pressure is between 1 and 30 bar, in the presence of a ruthenium-based catalyst. It will preferably be conducted at a low pressure of between 1 and 10 bar and more preferably at atmospheric pressure when the cross metathesis leads to formation of a light compound, as for example ethylene, in order to allow easy release thereof. The reaction may be conducted without solvent or in the presence of a solvent such as toluene, xylenes, or dichloromethane, benzene, chlorobenzene, or dimethyl carbonate.

Catalysis of the metathesis reaction has been a subject of a great number of studies, and the development of sophisticated catalytic systems. Mention may be made, for example, of the tungsten complexes developed by Schrock et al., (J. Am. Chem. Soc. 108 (1986) 2771) or Basset et al., Angew. Chem., Ed. Engl. 31 (1992) 628.

Having appeared more recently are catalysts known as Grubbs catalysts (Grubbs et al., Angew. Chem., Ed. Engl. 34 (1995) 2039 and Organic Letters 1 (1999) 953), which are ruthenium-benzylidene complexes operating in homogeneous catalysis.

Lastly, studies have led to the production of immobilized catalysts, these being catalysts in which the active principle is that of the homogeneous catalyst, particularly the ruthenium-carbene complexes, but which is immobilized on an inert support. The objective of these studies is to increase the selectivity of the cross metathesis reaction in relation to side-reactions such as "homo-metatheses" between the reactants brought together. The studies relate not only to the structure of the catalysts but also to the effect of the reaction medium and to the additives which may be introduced.

The metathesis reaction may therefore be carried out in the presence of a ruthenium catalyst chosen from charged or noncharged catalysts of general formula:

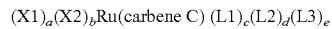

$(X1)_a(X2)_b Ru(\text{carbene C})(L1)_c(L2)_d(L3)_e$ in which:
a, b, c, d, and e are integers, identical or different, with a and b being 0, 1, or 2, and c, d, and e being 0, 1, 2, 3, or 4;

X1 and X2, which are identical or different, each represent a charged or noncharged unidentate or multidentate ligand; examples include halides, sulfate, carbonate, carboxylates, alkoxides, phenoxides, amides, tosylate, hexafluorophosphate, tetrafluoroborate, bis-triflylamide, an alkyl, tetraphenylborate, and derivatives. X1 or X2 may be bonded to (L1 or L2) or to the (carbene C) so as to form a bidentate or chelate ligand on the ruthenium; and L1, L2, and L3, which are identical or different, are electron-donating ligands such as phosphine, phosphite, phosphonite, phosphinite, arsine, stilbine, an olefin or an aromatic, a carbonyl compound, an ether, an alcohol, an amine, a pyridine or derivative, an imine, a thioether, or a heterocyclic carbene;

L1, L2, or L3 may be bonded to the (carbene C) so as to form a bidentate or chelate, or tridentate, ligand;

the (carbene C) is represented by the general formula: C_(R1)_(R2), for which R1 and R2 are identical or different groups such as hydrogen or any other saturated or unsaturated, cyclic, branched, or linear hydrocarbon group, or aromatic hydrocarbon group. Examples include the complexes of ruthenium with alkylidenes, benzylidene, or cumulenes such as vinylidenes, Ru=C=CHR, or allenylidenes, Ru=C=C=CR1R2, or indenylidenes.

A functional group allowing retention of the ruthenium complex in an ionic liquid may be grafted to at least one of the ligands X1, X2, L1, L2, or to the carbene C. This functional group may be charged or noncharged, such as, preferably, an ester, an ether, a thiol, an acid, an alcohol, an amine, a nitrogen-containing heterocycle, a sulfonate, a carboxylate, a quaternary ammonium, a guanidinium, a quaternary phosphonium, a pyridinium, an imidazolium, a morpholinium, or a sulfonium.

The metathesis catalyst may optionally be made heterogeneous, on a support, in order to facilitate its recovery/recycling.

The cross metathesis catalysts in the process of the invention are preferably ruthenium carbenes described, for example, in Aldrichimica Acta, vol. 40, No. 2, 2007, pp.

45-52. The preferred catalysts are the catalyst Umicore® M51 (sold by the company Umicore®) of formula (A) below, and the catalyst Umicore® M71 SIPr (sold by the company Umicore®) of formula (B) below, or else the catalysts sold by Materia®.

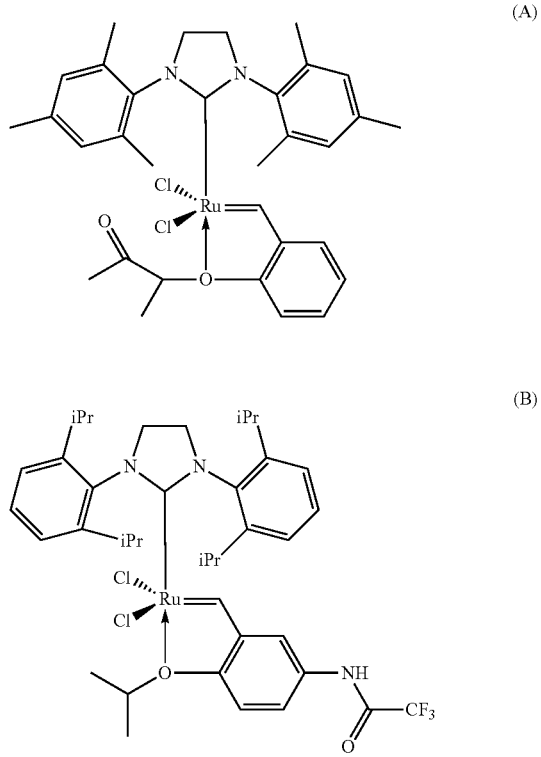

The reaction time is chosen according to the reactants and the operating conditions employed, and in order to reach the end of the reaction.

Since metathesis is an equilibrium reaction, it is appropriate to shift this equilibrium in order to approach total conversion. To do this when the coproduct of the reaction is a light olefin such as ethylene, it is easy to "degas" the reactor from time to time in order to force the removal of the light products and therefore to go to total conversion. Where the coproduct is a heavier, optionally functional, olefin, the extraction operation is less simple, insofar as it is necessary to maintain the two reactants and the catalyst in the reaction mixture. Moreover, if it is necessary at least partly to separate the unsaturated nitrile-ester (acid) by distillation and to remove the light compounds before hydrogenation, it is necessary to operate in a manner such that the metathesis catalyst remains in the heavy fraction with the nitrile-ester (acid), to use it in its function of hydrogenation catalyst. In this operation, at the separation stage, the very heavy compounds are not removed from the mixture, and will therefore be hydrogenated with the heavy fraction; their separation occurs during subsequent purification of the final amino acid/ester.

The other way of shifting the equilibrium is to use an excess of reactant; here, typically, an excess of acrylonitrile or of alkyl acrylate (methyl acrylate in general). From a process standpoint, the first step would be carried out to its end with exhaustion of the metathesis catalyst; the excess of acrylate or acrylonitrile would be distilled for recycling, and then, in a second step, the unsaturated α-ωnitrile-ester/acid compound present in the reaction mixture would be hydrogenated in the presence of the metal of the $1^{st}$-step catalyst in its hydrogenation function.

The amount of ruthenium metathesis catalyst introduced during the first step is chosen such that it ensures the whole of the possible conversion of the nonacrylic reactant present in the charge. It is observed that said catalyst, under the operating conditions of the metathesis step, is converted at the end of the reaction; it is exhausted or deactivated and loses its catalytic activity in terms of metathesis—it will be designated hereinafter by the attributive "degraded" for said reaction. In a batch process, the amount of catalyst may easily be adjusted in order to give the desired conversion at complete degradation of the catalyst.

At the end of the metathesis step, the reaction mixture is subjected to a hydrogenation. The hydrogenation reaction may be carried out directly on the reaction mixture obtained from the metathesis step and in the presence of the residual ruthenium metathesis catalyst acting as a hydrogenation catalyst. It may also be carried out with a conventional hydrogenation catalyst. The metals conventionally used for hydrogenation include nickel, palladium, platinum, rhodium, or iridium. The catalyst used will preferably be Raney nickel or palladium-on-carbon. The reaction is performed under hydrogen pressure and in the presence of a base. The pressure is between 5 and 100 bar, preferably between 20 and 30 bar. The temperature is between 50 and 150° C., preferably between 80 and 100° C. The base may be, for example, sodium hydroxide, potassium hydroxide, potassium tert-butoxide, or ammonia. The base is generally used in an amount of 10 to 80 mol % relative to the unsaturated nitrile-ester substrate.

The hydrogenation reaction may be carried out with or without solvent. In the case of a reaction in solvent medium, the preferred solvents used for the metathesis and hydrogenation steps are aromatic solvents such as toluene or xylenes, or a chlorinated solvent such as dichloromethane or chlorobenzene, or dimethyl carbonate.

The amino acids or amino esters obtained by the process of the invention may be used as monomers for the synthesis of polyamides.

The invention further provides the polymers obtained by polymerization of the α,ω-amino esters (acids) synthesized by the processes defined above.

The process of the invention is illustrated by the examples which follow.

EXAMPLE 1

Cross Metathesis of 10-Undecenenitrile with Methyl Acrylate in the Presence of Umicore® M71 SIPr Catalyst (B) after Treatment of the 10-Undecenitrile with Hydrazine 10-Undecenenitrile was prepared by reacting 10-undecenoic acid with ammonia in the presence of zinc oxide. The initial proportion of peroxide, determined by the method using potassium iodide and sodium thiosulfate, is 10 meq/kg.

A glass reactor purged with nitrogen is charged with 50 g of 10-undecenenitrile (containing 0.5 mmol of peroxides) and 30 mg of hydrazine monohydrate (0.6 mmol-1.2 equivalents). The mixture is heated at 50° C. for an hour with stirring.

The proportion of peroxide after treatment is less than 1 meq/kg. The product is used as it is for the metathesis reaction.

The metathesis reactor is a 250 ml jacketed glass reactor equipped with a magnetic stirrer, a condenser, a temperature probe, a nitrogen inlet, and a syringe driver for addition of the metathesis catalyst continuously. The nitrogen-purged reactor is charged with 5 g of 10-undecenenitrile purified beforehand (30 mmol), 5.2 g of methyl acrylate (60 mmol), and 50 g of toluene dried over molecular sieve. A syringe is charged with 1.2 mg of Umicore® M71 SIPr catalyst of formula (B) given above (catalyst supplied by the company Umicore®— $1.5 \times 10^{-3}$ mmol—0.005 mol % relative to the 10-undecenitrile) in solution in 5 ml of toluene. The system is heated to 100° C. and then the catalyst is added via the syringe driver over a period of 3 hours. The resulting reaction mixture is analyzed by gas chromatography to determine the conversion to 10-undecenenitrile and the selectivities for unsaturated $C_{12}$ nitrile-ester (product of cross metathesis) and for unsaturated $C_{20}$ dinitrile (product of self-metathesis).

The conversion of the 10-undecenenitrile is 89%. The selectivity for unsaturated $C_{12}$ nitrile-ester is 41%, and that for unsaturated $C_{20}$ dinitrile is 59%. The turnover number of the catalyst is 17 800.

At the outcome of a hydrogenation step following this metathesis step, an in-specification product (free from impurities) is obtained which can easily be polymerized, and with a better yield than in the comparative example below.

EXAMPLE 2 (COMPARATIVE)

The example was carried out under the same conditions as Example 1, without purification of the 10-undecenenitrile and using 0.0075 mol % of Umicore® M71 SIPr catalyst.

A the nitrogen-purged reactor is charged with 5 g of 10-undecenenitrile (not purified—30 mmol), 5.2 g of methyl acrylate (60 mmol), and 50 g of toluene dried over molecular sieve. A syringe is charged with 1.8 mg of Umicore M71 SIPr catalyst ($2.2 \times 10^{-3}$ mmol—0.0075 mol % relative to the 10-undecenitrile) in solution in 5 ml of toluene. The system is heated to 100° C. and then the catalyst is added via the syringe driver over a period of 3 hours.

The conversion of the 10-undecenenitrile is 5%. The turnover number of the catalyst is 666.

In the hydrogenation step, it is observed that the impurities present in a form combined with the ruthenium give rise to alcohols, to alcohol esters, and even to amino alcohol esters. In the polymerization step, these impurities act as chain-growth inhibitors, giving rise to the (difficult) production of a polymer of poor quality.

In summary, the thermal and/or chemical treatment of the process of the invention allows the impurities to be targeted and to be removed as early as possible, while limiting the loss of starting material, and therefore improving the selectivity of the metathesis step but also, surprisingly, all the steps downstream of the metathesis step, more particularly a hydrogenation step, and a step of optional polymerization of the monomer obtained by the process of the invention.

The invention claimed is:

1. A process for synthesizing a long-chain, saturated α,ω-amino ester (acid) having from 6 to 17 carbon atoms, said process comprising
    a first step of cross metathesis between a first, acrylic compound chosen from acrylonitrile, acrylic acid, or an acrylic ester, and a second, monounsaturated compound comprising at least one nitrile, acid, or ester functional group, one of these compounds comprising a nitrile function and the other an acid or ester function, in the presence of a ruthenium carbene metathesis catalyst, and
    a second step of hydrogenation of the resulting monounsaturated nitrile-ester (acid),
    wherein said monounsaturated compound comprising at least one nitrile, acid, or ester functional group has been purified beforehand by thermal and/or chemical treatment.

2. The synthesis process as claimed in claim 1, wherein said purification comprises thermal treatment, wherein said thermal treatment is carried out at a temperature of between 80° C. and 250° C.

3. The synthesis process as claimed in claim 2, wherein said purification comprises thermal treatment, wherein said thermal treatment is carried out without solvent under a nitrogen atmosphere.

4. The synthesis process as claimed in claim 1, wherein said purification comprises chemical treatment, wherein said chemical treatment comprises a step of adding a compound chosen from inorganic acids, bases, reducing agents, metals, metal salts, organic or inorganic compounds comprising ruthenium, and mixtures thereof.

5. The synthesis process as claimed in claim 1, wherein said purification comprises chemical treatment, wherein said chemical treatment is carried out without solvent or in a solvent which is subsequently used for the metathesis step.

6. The synthesis process as claimed in claim 4, wherein inorganic acids are added, wherein the inorganic acids are chosen from sulfuric acid, perchloric acid, hydrochloric acid, and mixtures thereof and are employed at a temperature of between 20 and 50° C.

7. The synthesis process as claimed in claim 4, wherein bases are added, wherein the bases are amines chosen from triethylamine, diethylamine, isobutylamine, triethanolamine, dimethylaniline, diethylaniline, dimethyl-para-toluidine, and mixtures thereof, and are employed at a temperature of between 20 and 120° C.

8. The synthesis process as claimed in claim 4, wherein reducing agents are added, wherein the reducing agents are chosen from trialkyl- and triarylphosphines, trialkyl or triaryl phosphites, inorganic or organic sulfides, hydrazine or alkyl- or arylhydrazines, hydroxylamine, formic acid, and mixtures thereof, and are employed at a temperature of between 20 and 50° C.

9. The synthesis process as claimed in claim 4, wherein metals are added, wherein the metals are chosen from alkali metals, alkaline earth metals, and rare earths, aluminum, titanium, zirconium, zinc, tin, lead, bismuth, iron, nickel, cobalt, copper, silver, and mixtures thereof, and are employed at a temperature of between 20 and 150° C.

10. The synthesis process as claimed in claim 4, wherein metal salts are added, wherein the metal salts are chosen from iron derivatives, cobalt derivatives, copper derivatives, manganese derivatives, nickel derivatives, and mixtures thereof, and are employed at a temperature of between 20 and 100° C.

11. The synthesis process as claimed in claim 1, wherein the metathesis catalyst conforms to one of the formulae (A) and (B) below:

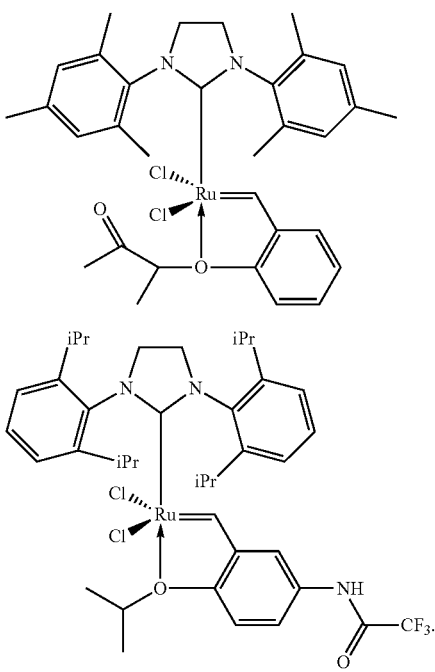

12. The synthesis process as claimed in claim 1, further comprising a step of polymerizing the resulting α,ω-amino ester (acid) for synthesis of a polymer.

13. The synthesis process as claimed in claim 2, wherein said thermal treatment is carried out at a temperature of between 80° C. and 180° C.

14. The synthesis process as claimed in claim 2, wherein said thermal treatment is carried out at a temperature of between 100 and 150° C.

15. The synthesis process as claimed in claim 10, wherein the iron derivatives are chosen from iron(II) acetate, iron(III) acetate, iron(II) acetylacetonate, iron(III) acetylacetonate; wherein the cobalt derivatives are chosen from cobalt(II) acetate, cobalt(II) acetylacetonate, cobalt(III) acetylacetonate, cobalt(II) 2-ethylhexanoate; wherein the copper derivatives are chosen from copper(I) acetate, copper(II) acetate, copper(I) acetylacetonate, copper(II) 2-ethylhexanoate; wherein the manganese derivatives are chosen from manganese(II) acetate, manganese(III) acetate, manganese(II) acetylacetonate, manganese(III) acetylacetonate; and wherein the nickel derivatives are chosen from nickel(II) acetate, nickel(II) acetylacetonate, nickel(II) 2-ethylhexanoate.

16. The synthesis process as claimed in claim 1, further comprising a step of polymerizing the resulting α,ω-amino ester (acid) for synthesis of a polyamide.

* * * * *